United States Patent
Levin et al.

(10) Patent No.: US 7,307,196 B2
(45) Date of Patent: *Dec. 11, 2007

(54) MOLECULAR SIEVE COMPOSITIONS, CATALYST THEREOF, THEIR MAKING AND USE IN CONVERSION PROCESSES

(75) Inventors: Doron Levin, Annandale, NJ (US); James Clark Vartuli, Schwenksville, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/910,739

(22) Filed: Aug. 3, 2004

(65) Prior Publication Data

US 2005/0255991 A1 Nov. 17, 2005

Related U.S. Application Data

(62) Division of application No. 10/364,156, filed on Feb. 10, 2003, now Pat. No. 6,844,291.

(60) Provisional application No. 60/360,963, filed on Feb. 28, 2002, provisional application No. 60/366,012, filed on Mar. 20, 2002.

(51) Int. Cl.
*C07C 1/20* (2006.01)
*C07C 1/00* (2006.01)
*C07C 5/333* (2006.01)

(52) U.S. Cl. ............... 585/639; 585/638; 585/640; 585/648; 585/653; 585/641; 585/642

(58) Field of Classification Search ............ 585/638, 585/639, 640, 648, 653, 641, 642
See application file for complete search history.

(56) References Cited

U.S. PATENT DOCUMENTS

| | | | | |
|---|---|---|---|---|
| 4,025,572 A | * | 5/1977 | Lago | 585/408 |
| 4,062,905 A | | 12/1977 | Chang et al. | |
| 4,079,095 A | | 3/1978 | Givens et al. | |
| 4,112,056 A | * | 9/1978 | Chen et al. | 423/704 |
| 4,310,440 A | | 1/1982 | Wilson et al. | |
| 4,440,871 A | | 4/1984 | Lok et al. | |
| 4,465,889 A | | 8/1984 | Anthony et al. | 585/640 |
| 4,499,327 A | * | 2/1985 | Kaiser | 585/640 |
| 4,677,242 A | | 6/1987 | Kaiser | |
| 4,677,243 A | | 6/1987 | Kaiser | |
| 4,873,390 A | | 10/1989 | Lewis et al. | |
| 5,095,163 A | | 3/1992 | Barger | |
| 5,346,875 A | | 9/1994 | Wachter et al. | 502/233 |
| 5,367,100 A | | 11/1994 | Gongwei et al. | |
| 5,714,662 A | | 2/1998 | Vora et al. | |
| 6,166,282 A | | 12/2000 | Miller | |
| 6,228,799 B1 | | 5/2001 | Aubert et al. | 502/304 |
| 2001/0002383 A1 | | 5/2001 | Hidaka et al. | 502/72 |
| 2002/0013505 A1 | | 1/2002 | Fung et al. | 585/640 |
| 2002/0119887 A1 | | 8/2002 | Huo et al. | 502/60 |
| 2003/0004056 A1 | | 1/2003 | Mees et al. | 502/208 |
| 2003/0171633 A1 | | 9/2003 | Xu et al. | 585/640 |
| 2003/0176753 A1 | | 9/2003 | Levin et al. | 585/640 |
| 2003/0181322 A1 | | 9/2003 | Chang et al. | 502/214 |
| 2003/0187312 A1 | | 10/2003 | Chang et al. | 585/500 |

FOREIGN PATENT DOCUMENTS

| | | |
|---|---|---|
| EP | 0 256 875 | 2/1988 |
| EP | 0 697 247 | 7/1995 |
| EP | 0 923 512 | 6/1999 |
| EP | 0 993 867 | 4/2000 |
| EP | 0 906 244 | 1/2002 |
| JP | 2001028216 | 4/1999 |
| WO | WO 00/69796 | 11/2000 |

OTHER PUBLICATIONS

W. J. Mortier, *Zeolite Electronegativity Related to Physicochemical Properties*, Journal of Catalysis, vol. 55, pp. 138-145, (Jun. 1978).
Tseng et al., Isosynthesis Reactions of CO/H2 Over Zirconium Dioxide, Journal of Catalysis, vol. 109, pp. 284-297, (Sep. 1987).
Gerhartz, W. and Yamamota, Y.S., "Ullman's Encyclopedia of Industrial Chemistry, vol. A7; Edition 5", 1986, VCH VERLAG, Weinheim, DE, XP002252573, p. 128, Table 2, no month.

* cited by examiner

*Primary Examiner*—Elizabeth D. Wood

(57) ABSTRACT

The invention relates to a catalyst composition, a method of making the same and its use in the conversion of a feedstock, preferably an oxygenated feedstock, into one or more olefin(s), preferably ethylene and/or propylene The catalyst composition comprises a molecular sieve and at least one oxide of a metal from Group 4, optionally in combination with at least one metal from Groups 2 and 3, of the Periodic Table of Elements.

26 Claims, No Drawings

MOLECULAR SIEVE COMPOSITIONS, CATALYST THEREOF, THEIR MAKING AND USE IN CONVERSION PROCESSES

CROSS REFERENCE TO RELATED APPLICATIONS

This application is a divisional of U.S. application Ser. No. 10/364,156, filed Feb. 10, 2003, and now U.S. Pat. No. 6,844,291, which claims priority under 35 U.S.C. 120 from U.S. Provisional Patent Application Ser. No. 60/360,963, filed Feb. 28, 2002 and from U.S. Provisional Patent Application Ser. No. 60/366,012, filed Mar. 20, 2002, the entire contents of which applications are incorporated herein by reference.

FIELD

The present invention relates to molecular sieve compositions and catalysts containing the same, to the synthesis of such compositions and catalysts and to the use of such compositions and catalysts in conversion processes to produce olefin(s).

BACKGROUND

Olefins are traditionally produced from petroleum feedstocks by catalytic or steam cracking processes. These cracking processes, especially steam cracking, produce light olefin(s), such as ethylene and/or propylene, from a variety of hydrocarbon feedstocks. Ethylene and propylene are important commodity petrochemicals useful in a variety of processes for making plastics and other chemical compounds.

The petrochemical industry has known for some time that oxygenates, especially alcohols, are convertible into light olefin(s). There are numerous technologies available for producing oxygenates including fermentation or reaction of synthesis gas derived from natural gas, petroleum liquids or carbonaceous materials including coal, recycled plastics, municipal waste or any other organic material. Generally, the production of synthesis gas involves a combustion reaction of natural gas, mostly methane, and an oxygen source into hydrogen, carbon monoxide and/or carbon dioxide. Other known syngas production processes include conventional steam reforming, autothermal reforming, or a combination thereof.

Methanol, the preferred alcohol for light olefin production, is typically synthesized from the catalytic reaction of hydrogen, carbon monoxide and/or carbon dioxide in a methanol reactor in the presence of a heterogeneous catalyst. For example, in one synthesis process methanol is produced using a copper/zinc oxide catalyst in a water-cooled tubular methanol reactor. The preferred process for converting a feedstock containing methanol into one or more olefin(s), primarily ethylene and/or propylene, involves contacting the feedstock with a molecular sieve catalyst composition.

Molecular sieves are porous solids having pores of different sizes such as zeolites or zeolite-type molecular sieves, carbons and oxides. The most commercially useful molecular sieves for the petroleum and petrochemical industries are known as zeolites, for example aluminosilicate molecular sieves. Zeolites in general have a one-, two- or three-dimensional crystalline pore structure having uniformly sized pores of molecular dimensions that selectively adsorb molecules that can enter the pores, and exclude those molecules that are too large.

There are many different types of molecular sieve well known to convert a feedstock, especially an oxygenate containing feedstock, into one or more olefin(s). For example, U.S. Pat. No. 5,367,100 describes the use of the zeolite, ZSM-5, to convert methanol into olefin(s); U.S. Pat. No. 4,062,905 discusses the conversion of methanol and other oxygenates to ethylene and propylene using crystalline aluminosilicate zeolites, for example Zeolite T, ZK5, erionite and chabazite; U.S. Pat. No. 4,079,095 describes the use of ZSM-34 to convert methanol to hydrocarbon products such as ethylene and propylene; and U.S. Pat. No. 4,310,440 describes producing light olefin(s) from an alcohol using a crystalline aluminophosphate, often designated $AlPO_4$.

Some of the most useful molecular sieves for converting methanol to olefin(s) are silicoaluminophosphate molecular sieves. Silicoaluminophosphate (SAPO) molecular sieves contain a three-dimensional microporous crystalline framework structure of $[SiO_4]$, $[AlO_4]$ and $[PO_4]$ corner sharing tetrahedral units. SAPO synthesis is described in U.S. Pat. No. 4,440,871, which is herein fully incorporated by reference. SAPO molecular sieves are generally synthesized by the hydrothermal crystallization of a reaction mixture of silicon-, aluminum- and phosphorus-sources and at least one templating agent. Synthesis of a SAPO molecular sieve, its formulation into a SAPO catalyst, and its use in converting a hydrocarbon feedstock into olefin(s), particularly where the feedstock is methanol, are disclosed in U.S. Pat. Nos. 4,499,327, 4,677,242, 4,677,243, 4,873,390, 5,095,163, 5,714,662 and 6,166,282, all of which are herein fully incorporated by reference.

Typically, molecular sieves are formed into molecular sieve catalyst compositions to improve their durability in commercial conversion processes. These molecular sieve catalyst compositions are formed by combining the molecular sieve and a matrix material usually in the presence of a binder. The purpose of the binder is hold the matrix material, often a clay, to the molecular sieve.

Although it is known to use binders and matrix materials to form molecular sieve catalyst compositions useful in converting oxygenates into olefin(s), these binders and matrix materials typically only serve to provide desired physical characteristics to the catalyst composition, and have little to no effect on conversion and selectivity of the molecular sieve. It would therefore be desirable to have an improved molecular sieve catalyst composition having a better conversion rate, improved olefin selectivity and a longer lifetime.

U.S. Pat. No. 4,465,889 describes a catalyst composition comprising a silicalite molecular sieve impregnated with a thorium, zirconium, or titanium metal oxide for use in converting methanol, dimethyl ether, or a mixture thereof into a hydrocarbon product rich in iso-$C_4$ compounds.

U.S. Pat. No. 6,180,828 discusses the use of a modified molecular sieve to produce methylamines from methanol and ammonia, where for example, a silicoaluminophosphate molecular sieve is combined with one or more modifiers, such as a zirconium oxide, a titanium oxide, an yttrium oxide, montmorillonite or kaolinite.

U.S. Pat. No. 5,417,949 relates to a process for converting noxious nitrogen oxides in an oxygen containing effluent into nitrogen and water using a molecular sieve and a metal oxide binder, where the preferred binder is titania and the molecular sieve is an aluminosilicate.

EP-A-312981 discloses a process for cracking vanadium-containing hydrocarbon feed streams using a catalyst composition comprising a physical mixture of a zeolite embedded in an inorganic refractory matrix material and at least one oxide of beryllium, magnesium, calcium, strontium, barium or lanthanum, preferably magnesium oxide, on a silica-containing support material.

Kang and Inui, *Effects of decrease in number of acid sites located on the external surface of Ni-SAPO-34 crystalline catalyst by the mechanochemical method*, Catalysis Letters 53, pages 171–176 (1998) disclose that the shape selectivity can be enhanced and the coke formation mitigated in the conversion of methanol to ethylene over Ni-SAPO-34 by milling the catalyst with MgO, CaO, BaO or $Cs_2O$ on microspherical non-porous silica, with BaO being the most preferred.

International Publication No. WO 98/29370 discloses the conversion of oxygenates to olefins over a small pore non-zeolitic molecular sieve containing a metal selected from the group consisting of a lanthanide, an actinide, scandium, yttrium, a Group 4 metal, a Group 5 metal or combinations thereof.

SUMMARY

In one aspect, the invention resides in a catalyst composition comprising a molecular sieve and at least one oxide of a metal selected from Group 4 of the Periodic Table of Elements, wherein said metal oxide has an uptake of carbon dioxide at 100° C. of at least 0.03, and typically at least 0.035, $mg/m^2$ of the metal oxide.

The catalyst composition may also include at least one of a binder and a matrix material different from said metal oxide.

The catalyst composition may also include an oxide of a metal selected from Group 2 and Group 3 of the Periodic Table of Elements. In one embodiment, the Group 4 metal oxide comprises zirconium oxide and the Group 2 and/or Group 3 metal oxide comprises one or more oxides selected from calcium oxide, barium oxide, lanthanum oxide, yttrium oxide and scandium oxide.

The molecular sieve conveniently comprises a framework including at least two tetrahedral units selected from $[SiO_4]$, $[AlO_4]$ and $[PO_4]$ units, such as a silicoaluminophosphate.

In another aspect, the invention resides in a molecular sieve catalyst composition comprising an active Group 4 metal oxide and a Group 2 and/or a Group 3 metal oxide, a binder, a matrix material, and a silicoaluminophosphate molecular sieve.

In another aspect, the invention resides in a method for making a catalyst composition, the method comprising the step of physically mixing first particles comprising a molecular sieve with second particles comprising a Group 4 metal oxide having an uptake of carbon dioxide at 100° C. of at least 0.03 $mg/m^2$ of the metal oxide particles.

In one embodiment, the molecular sieve, a binder and a matrix material are made into a formulated molecular sieve catalyst composition that is then contacted, mixed, combined, spray dried, or the like, with an active Group 4 metal oxide, such as an active zirconium metal oxide and/or an active hafnium metal oxide, optionally in the presence of a Group 2 and/or a Group 3 metal oxide.

In another aspect, the invention resides in a method of making a catalyst composition, the method comprising:
(i) synthesizing a molecular sieve from a reaction mixture comprising at least one templating agent and at least two of a silicon source, a phosphorus source and an aluminum source; and
(ii) recovering the molecular sieve synthesized in step (i);
(iii) forming a hydrated precursor to a Group 4 metal oxide by precipitation from a solution containing a source of Group 4 metal metal ions;
(iv) recovering the hydrated precursor formed in step (iii);
(v) calcining the hydrated precursor recovered in step (iv) to form a calcined metal oxide that has an uptake of carbon dioxide at 100° C. of at least 0.03 $mg/m^2$ of the metal oxide; and
(vi) physically mixing the molecular sieve recovered in step (i) and the calcined metal oxide of step (v).

In yet another aspect, the invention is directed to a process for producing olefin(s) by converting a feedstock, such as an oxygenate, conveniently an alcohol, for example methanol, in the presence of any of the above molecular sieve compositions and/or molecular sieve or formulated molecular sieve catalyst compositions.

In yet another aspect, the invention is directed to a process for converting a feedstock into one or more olefin(s) in the presence of a molecular sieve catalyst composition comprising a molecular sieve, a binder, a matrix material and a mixture of metal oxides different from the binder and the matrix material.

In one embodiment, the catalyst composition has a Lifetime Enhancement Index (LEI) greater than 1, such as greater than 1.5. LEI is defined herein as the ratio of the lifetime of the catalyst composition to that of the same catalyst composition in the absence of an active metal oxide.

DETAILED DESCRIPTION OF THE EMBODIMENTS

Introduction

The invention is directed to a molecular sieve catalyst composition and to its use in the conversion of hydrocarbon feedstocks, particularly oxygenated feedstocks, into olefin(s). It has been found that combining a molecular sieve with one or more active metal oxides results in a catalyst composition with an enhanced olefin yield and/or a longer lifetime when used in the conversion of feedstocks, such as oxygenates, more particularly methanol, into olefin(s). In addition, the resultant catalyst composition tends to be more propylene selective and to yield lower amounts of unwanted ethane and propane, together with other undesirable compounds, such as aldehydes and ketones, specifically acetaldehyde.

The preferred active metal oxides are those having a Group 4 metal (for example zirconium and hafnium) from the Periodic Table of Elements using the IUPAC format described in the *CRC Handbook of Chemistry and Physics*, 78th Edition, CRC Press, Boca Raton, Fla. (1997). In some cases, it is found that improved results are obtained when the catalyst composition also contains at least one oxide of a metal selected from Group 2 and/or Group 3 of the Periodic Table of Elements.

Molecular Sieves

Molecular sieves have been classified by the Structure Commission of the International Zeolite Association according to the rules of the IUPAC Commission on Zeolite Nomenclature. According to this classification, framework-type zeolite and zeolite-type molecular sieves, for which a structure has been established, are assigned a three letter code and are described in the *Atlas of Zeolite Framework Types,* 5th edition, Elsevier, London, England (2001), which is herein fully incorporated by reference.

Crystalline molecular sieves all have a 3-dimensional, four-connected framework structure of corner-sharing $[TO_4]$ tetrahedra, where T is any tetrahedrally coordinated cation. Molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1–67, Elsevier Science, B.V., Amsterdam, Netherlands (2001).

Non-limiting examples of molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEO, PER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of preferred molecular sieves, particularly for converting an oxygenate containing feedstock into olefin(s), include AEL, AFY, AEI, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

The small, medium and large pore molecular sieves have from a 4-ring to a 12-ring or greater framework-type. In a preferred embodiment, the zeolitic molecular sieves have 8-, 10- or 12-ring structures and an average pore size in the range of from about 3 Å to 15 Å. In a more preferred embodiment, the molecular sieves, preferably silicoaluminophosphate molecular sieves, have 8-rings and an average pore size less than about 5 Å, such as in the range of from 3 Å to about 5 Å, for example from 3 Å to about 4.5 Å, and particularly from 3.5 Å to about 4.2 Å.

Molecular sieves have a molecular framework of one, preferably two or more corner-sharing [TO4] tetrahedral units, more preferably, two or more [SiO$_4$], [AlO$_4$] and/or [PO$_4$] tetrahedral units, and most preferably [SiO$_4$], [AlO$_4$] and [PO$_4$] tetrahedral units. These silicon, aluminum, and phosphorus based molecular sieves and metal containing derivatives thereof have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO$_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6.156.931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO$_2$]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in R. Szostak *Handbook of Molecular Sieves*, Van Nostrand Reinhold, New York, N.Y. (1992), which is herein fully incorporated by reference.

The more preferred molecular sieves include aluminophosphate (AlPO) molecular sieves and silicoaluminophosphate (SAPO) molecular sieves and substituted, preferably metal substituted, AlPO and SAPO molecular sieves. The most preferred molecular sieves are SAPO molecular sieves, and metal substituted SAPO molecular sieves. in an embodiment, the metal is an alkali metal of Group 1 of the Periodic Table of Elements, an alkaline earth metal of Group 2 of the Periodic Table of Elements, a rare earth metal of Group 3 of the Periodic Table of Elcments, including the Lanthanides: lanthanum, cerium, praseodymiwn, neodymium, samarium, europium, gadolinium, terbium, dysprosium, holmium, erbium, thulium, yttcrbium and lutetium; and scandium or yttrium, a transition metal of Groups 4 to 12 of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. Patents mentioned above, is represented by the empirical formula, on an anhydrous basis:

$$mR:(M_xAl_yP_z)O_2$$

wherein R represents at lcast one templating agent, preferably an organic templating agent; m is the number of moles of R per mole of $(M_xAl_yP_z)O_2$ and has a value from 0 to 1, preferably 0 to 0.5, and most preferably from 0 to 0.3; x, y, and z represent the mole fraction of Al, P and M as tetrahedral oxides, where M is a metal selected from one of Groups 1, 2, 3, 4, 5, 6, 7, 8, 9, 10, 11, 12, 13, 14 and Lanthanide's of the Periodic Table of Elements, preferably M is selected from one of the group consisting of Si, Co, Cr, Cu, Fc, Ga, Ge, Mg, Mn, Ni, Sn, Ti, Zn and Zr. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and AlPO molecular sieves useful herein include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, AlPO-5, AlPO-11, AlPO-18, AlPO-31, AlPO-34, AlPO-36, AlPO-37, AlPO-46, and metal containing molecular sieves thereof. Of these, particularly useful molecular sieves are one or a combination of SAPO-18, SAPO-34, SAPO-35, SAPO-44, SAPO-56, AlPO-18 and AlPO-34 and metal containing derivatives thereof, such as one or a combination of SAPO-18, SAPO-34, AlPO-34 and AlPO-18, and metal containing derivatives thereof, and especially one or a combination of SAPO-34 and AlPO-18, and metal containing derivatives thereof.

In an embodiment, the molecular sieve is an intergrowth material having two or more distinct crystalline phases within one molecular sieve composition. In particular, intergrowth molecular sieves are described in the U.S. patent application Ser. No. 09/924,016 filed Aug. 7,2001 and International Publication No. WO 98/15496 published Apr. 16, 1998, both of which are herein fully incorporated by reference. For example, SAPO-18, AlPO-18 and RUW-18 have an AEI framework-type, and SAPO-34 has a CHA framework-type. Thus the molecular sieve used herein may comprise at least one intergrowth phase of AEI and CHA framework-types, especially where the ratio of CHA framework-type to AEI framework-type, as determined by the DIFFaX method disclosed in U.S. patent application Ser. No. 09/924,106 filed Aug. 7, 2001, is greater than 1:1.

Molecular Sieve Synthesis

The synthesis of molecular sieves is described in many of the references discussed above. Generally, molecular sieves are synthesized by the hydrothermal crystallization of one or more of a source of aluminum, a source of phosphorus, a source of silicon and a templating agent, such as a nitrogen containing organic compound. Typically, a combination of sources of silicon, aluminum and phosphorus, optionally with one or more templating agents, is placed in a sealed pressure vessel, optionally lined with an inert plastic such as polytetrafluoroethylene, and heated, under a crystallization pressure and temperature, until a crystalline material is formed, and then recovered by filtration, centrifugation and/or decanting.

Non-limiting examples of silicon sources include silicates, fumed silica, for example, Aerosil-200 available from Degussa Inc., New York, N.Y., and CAB-O-SIL M-5, organosilicon compounds such as tetraalkyl orthosilicates, for example, tetramethyl orthosilicate (TMOS) and tetraethylorthosilicate (TEOS), colloidal silicas or aqueous suspensions thereof, for example Ludox HS40 sol available from E.I. du Pont de Nemours, Wilmington, De., silicic acid or any combination thereof.

Non-limiting examples of aluminum sources include aluminum alkoxides, for example aluminum isopropoxide, aluminum phosphate, aluminum hydroxide, sodium aluminate, pseudo-boehmite, gibbsite and aluminum trichloride, or any combination thereof. A convenient source of aluminum is pseudo-boehmite, particularly when producing a silicoaluminophosphate molecular sieve.

Non-limiting examples of phosphorus sources, which may also include aluminum-containing phosphorus compositions, include phosphoric acid, organic phosphates such as triethyl phosphate, and crystalline or amorphous aluminophosphates such as $AlPO_4$, phosphorus salts, or combinations thereof. A convenient source of phosphorus is phosphoric acid, particularly when producing a silicoaluminophosphate.

Templating agents are generally compounds that contain elements of Group 15 of the Periodic Table of Elements, particularly nitrogen, phosphorus, arsenic and antimony. Typical templating agents also contain at least one alkyl or aryl group, such as an alkyl or aryl group having from 1 to 10 carbon atoms, for example from 1 to 8 carbon atoms. Preferred templating agents are often nitrogen-containing compounds, such as amines, quaternary ammonium compounds and combinations thereof. Suitable quaternary ammonium compounds are represented by the general formula $R_4N^+$, where each R is hydrogen or a hydrocarbyl or substituted hydrocarbyl group, preferably an alkyl group or an aryl group having from 1 to 10 carbon atoms.

Non-limiting examples of templating agents include tetraalkyl ammonium compounds including salts thereof, such as tetramethyl ammonium compounds, tetraethyl ammonium compounds, tetrapropyl ammonium compounds, and tetrabutylammonium compounds, cyclohexylamine, morpholine, di-n-propylamine (DPA), tripropylamine, triethylamine (TEA), triethanolamine, piperidine, cyclohexylamine, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo(2,2,2)octane, N',N',N,N-tetramethyl-(1,6) hexanediamine, N-methyldiethanolamine, N-methyl-ethanolamine, N-methyl piperidine, 3-methyl-piperidine, N-methylcyclohexylamine, 3-methylpyridine, 4-methyl-pyridine, quinuclidine, N,N'-dimethyl-1,4-diazabicyclo(2,2,2) octane ion; di-n-butylamine, neopentylamine, di-n-pentylamine, isopropylamine, t-butyl-amine, ethylenediamine, pyrrolidine, and 2-imidazolidone.

The pH of the synthesis mixture containing at a minimum a silicon-, aluminum-, and/or phosphorus-composition, and a templating agent, is generally in the range of from 2 to 10, such as from 4 to 9, for example from 5 to 8.

Generally, the synthesis mixture described above is sealed in a vessel and heated, preferably under autogenous pressure, to a temperature in the range of from about 80° C. to about 250° C., such as from about 100° C. to about 250° C., for example from about 125° C. to about 225° C., such as from about 150° C. to about 180° C.

In one embodiment, the synthesis of a molecular sieve is aided by seeds from another or the same framework type molecular sieve.

The time required to form the crystalline product is usually dependent on the temperature and can vary from immediately up to several weeks. Typically the crystallization time is from about 30 minutes to around 2 weeks, such as from about 45 minutes to about 240 hours, for example from about 1 hour to about 120 hours. The hydrothermal crystallization may be carried out with or without agitation or stirring.

Once the crystalline molecular sieve product is formed, usually in a slurry state, it may be recovered by any standard technique well known in the art, for example, by centrifugation or filtration. The recovered crystalline product may then be washed, such as with water, and then dried, such as in air.

One method for crystallization involves producing an aqueous reaction mixture containing an excess amount of a templating agent, subjecting the mixture to crystallization under hydrothermal conditions, establishing an equilibrium between molecular sieve formation and dissolution, and then, removing some of the excess templating agent and!or organic base to inhibit dissolution of the molecular sieve. See for example U.S. Pat. No. 5,296,208, which is herein fully incorporated by reference.

Other methods for synthesizing molecular sieves or modifying molecular sieves are described in U.S. Pat. No. 5,879, 655 (controlling the ratio of the templating agent to phosphorus), U.S. Pat. No. 6,005,155 (use of a modifier without a salt), U.S. Pat. No. 5,475,182 (acid extraction), U.S. Pat. No. 5,962,762 (treatment with transition metal), U.S. Pat. Nos. 5,925,586 and 6,153,552 (phosphorus modified), U.S. Pat. No. 5,925,800 (monolith supported), U.S. Pat. No. 5,932,512 (fluorine treated), U.S. Pat. No. 6,046,373 (electromagnetic wave treated or modified), U.S. Pat. No. 6,051,746 (polynuclear aromatic modifier), U.S. Pat. No. 6,225,254 (heating template), PCT WO 01/36329 published May 25, 2001 (surfactant synthesis), PCT WO 01/25151 published Apr. 12, 2001 (staged acid addition), PCT WO 01/60746 published Aug. 23, 2001 (silicon oil), U.S. patent application Ser. No. 09/929,949 filed Aug. 15, 2001 (cooling molecular sieve), U.S. patent application Ser. No. 09/615,526 filed Jul. 13, 2000 (metal impregnation including copper), U.S. patent application Ser. No. 09/672,469 filed Sep. 28, 2000 (conductive microfilter), and U.S. patent application Ser. No. 09/754,812 filed Jan. 4, 2001(freeze drying the molecular sieve), which are all herein fully incorporated by reference.

Where a templating agent is used in the synthesis of the molecular sieve, any templating agent retained in the product may be removed after crystallization by numerous well known techniques, for example, by calcination. Calcination involves contacting the molecular sieve containing the templating agent with a gas, preferably containing oxygen, at any desired concentration at an elevated temperature sufficient to either partially or completely remove the templating agent.

Aluminosilicate and silicoaluminophosphate molecular sieves have either a high silicon (Si) to aluminum (Al) ratio or a low silicon to aluminum ratio, however, a low Si/Al ratio is preferred for SAPO synthesis. In one embodiment, the molecular sieve has a Si/Al ratio less than 0.65, such as less than 0.40, for example less than 0.32, and particularly less than 0.20. In another embodiment the molecular sieve has a Si/Al ratio in the range of from about 0.65 to about 0.10, such as from about 0.40 to about 0.10, for example from about 0.32 to about 0.10, and particularly from about 0.32 to about 0.15.

Active Metal Oxides

Active metal oxides useful herein are those metal oxides, different from typical binders and/or matrix materials, that, when used in combination with a molecular sieve, provide benefits in catalytic conversion processes. Preferred active metal oxides are those metal oxides having a Group 4 metal, such as zirconium and/or hafnium, either alone or in combination with a Group 2 (for example magnesium, calcium, strontium and barium) and/or a Group 3 metal (including the Lanthanides and Actinides) oxide (for example yttrium, scandium and lanthanum). The most preferred active Group 4 metal oxide is an active zirconium metal oxide, either alone or in combination with calcium oxide, barium oxide, lanthanum oxide and/or yttrium oxide. In general, oxides of silicon, aluminum, and combinations thereof are not preferred.

In one embodiment, active metal oxides are those metal oxides, different from typical binders and/or matrix materials that, when used in combination with a molecular sieve in a catalyst composition, are effective in extending of the useful life of the catalyst composition. Quantification of the extension in catalyst life is determined by the Lifetime Enhancement Index (LEI) as defined by the following equation:

$$LEI = \frac{\text{Lifetime of Catalyst in Combination with Active Metal Oxide}}{\text{Lifetime of Catalyst}}$$

where the lifetime of the catalyst or catalyst composition, in the same process under the same conditions, is the cumulative amount of feedstock processed per gram of catalyst composition until the conversion of feedstock by the catalyst composition falls below some defined level, for example 10%. An inactive metal oxide will have little to no effect on the lifetime of the catalyst composition, or will shorten the lifetime of the catalyst composition, and will therefore have a LEI less than or equal to 1. Thus active metal oxides of the invention are those metal oxides, different from typical binders and/or matrix materials, that, when used in combination with a molecular sieve, provide a molecular sieve catalyst composition that has a LEI greater than 1. By definition, a molecular sieve catalyst composition that has not been combined with an active metal oxide will have a LEI equal to 1.0.

It is found that, by including an active metal oxide in combination with a molecular sieve, a catalyst composition can be produced having an LEI in the range of from greater than 1 to 20, such as from about 1.5 to about 10. Typically catalyst compositions according to the invention exhibit LEI values greater than 1.1, for example in the range of from about 1.2 to 15, and more particularly greater than 1.3, such as greater than 1.5, such as greater than 1.7, such as greater than 2.

In one embodiment, the active metal oxide when combined with a molecular sieve in a catalyst composition enhances the lifetime of the catalyst composition in the conversion of a feedstock comprising methanol, preferably into one or more olefin(s).

In particular, the metal oxides useful herein have an uptake of carbon dioxide at 100° C. of at least 0.03 mg/m² of the metal oxide, such as at least 0.035 mg/m² of the metal oxide. Although the upper limit on the carbon dioxide uptake of the metal oxide is not critical, in general the metal oxides useful herein will have a carbon dioxide at 100° C. of less than 10 mg/m² of the metal oxide, such as less than 5 mg/m² of the metal oxide. Typically, the metal oxides useful herein have a carbon dioxide uptake of 0.04 to 0.2 mg/m² of the metal oxide.

In order to determine the carbon dioxide uptake of a metal oxide, the following procedure is adopted. A sample of the metal oxide is dehydrated by heating the sample to about 200° C. to 500° C. in flowing air until a constant weight, the "dry weight", is obtained. The temperature of the sample is then reduced to 100° C. and carbon dioxide is passed over the sample, either continuously or in pulses, again until constant weight is obtained. The increase in weight of the sample in terms of mg/mg of the sample based on the dry weight of the sample is the amount of adsorbed carbon dioxide.

In the Examples reported below, the carbon dioxide adsorption is measured using a Mettler TGA/SDTA 851 thermogravimetric analysis system under ambient pressure. The metal oxide sample is dehydrated in flowing air to about 500° C. for one hour. The temperature of the sample is then reduced in flowing helium to 100° C. After the sample has equilibrated at the desired adsorption temperature in flowing helium, the sample is subjected to 20 separate pulses (about 12 seconds/pulse) of a gaseous mixture comprising 10-weight % carbon dioxide with the remainder being helium. After each pulse of the adsorbing gas the metal oxide sample is flushed with flowing helium for 3 minutes. The increase in weight of the sample in terms of mg/mg adsorbent based on the adsorbent weight after treatment at 500° C. is the amount of adsorbed carbon dioxide. The surface area of the sample is measured in accordance with the method of Brunauer, Emmett, and Teller (BET) published as ASTM D 3663 to provide the carbon dioxide uptake in terms of mg carbon dioxide/$m^2$ of the metal oxide.

In one embodiment, the active metal oxide(s) has a BET surface area of greater than 10 $m^2/g$, such as greater than 10 $m^2/g$ to about 300 $m^2/g$. In another embodiment, the active metal oxide(s) has a BET surface area greater than 20 $m^2/g$, such as from 20 $m^2/g$ to 250 $m^2/g$. In yet another embodiment, the active metal oxide(s) has a BET surface area greater than 25 $m^2/g$, such as from 25 $m^2/g$ to about 200 $m^2/g$. In a preferred embodiment, the active metal oxide(s) includes a zirconium oxide having a BET surface area greater than 20 $m^2/g$, such as greater than 25 $m^2/g$ and particularly greater than 30 $m^2/g$ The active metal oxide(s) used herein can be prepared using a variety of methods. It is preferable that the active metal oxide is made from an active metal oxide precursor, such as a metal salt, such as a halide, nitrate sulfate or acetate. Other suitable sources of the metal oxide include compounds that form the metal oxide during calcination, such as oxychlorides and nitrates. Alkoxides are also suitable sources of the Group 4 metal oxide, for example zirconium n-propoxide. A preferred source of the Group 4 metal oxide is hydrated zirconia. The expression, hydrated zirconia, is intended to connote a material comprising zirconium atoms covalently linked to other zirconium atoms via bridging oxygen atoms, and further comprising available hydroxyl groups.

In one embodiment, the hydrated zirconia is hydrothermally treated under conditions that include a temperature of at least 80° C., preferably at least 100° C. The hydrothermal treatment typically takes place in a sealed vessel at greater than atmospheric pressure. However, a preferred mode of treatment involves the use of an open vessel under reflux conditions. Agitation of hydrated Group 4 metal oxide in a liquid medium, for example, by the action of refluxing liquid and/or stirring, promotes the effective interaction of the hydrated oxide with the liquid medium. The duration of the contact of the hydrated oxide with the liquid medium is conveniently at least 1 hour, such as at least 8 hours. The liquid medium for this treatment typically has a pH of about 6 or greater, such as 8 or greater. Non-limiting examples of suitable liquid media include water, hydroxide solutions (including hydroxides of $NH_4^+$, $Na^+$, $K^+$, $Mg^{2+}$, and $Ca^{2+}$), carbonate and bicarbonate solutions (including carbonates and bicarbonates of $NH_4^+$, $Na^+$, $K^+$, $Mg^{2+}$, and $Ca^{2+}$), pyridine and its derivatives, and alkyl/hydroxyl amines.

In another embodiment, the active metal oxide is prepared, for example, by subjecting a liquid solution, such as an aqueous solution, comprising a source of ions of a Group 4 metal to conditions sufficient to cause precipitation of a hydrated precursor of the solid oxide material, such as by the addition of a precipitating reagent to the solution. Conveniently, the precipitation is conducted at a pH above 7. For example, the precipitating agent may be a base such as sodium hydroxide or ammonium hydroxide.

When a mixture of a Group 4 metal oxide with a Group 2 and/or 3 metal oxide is to be prepared, a first liquid solution comprising a source of ions of a Group 4 metal can be combined with a second liquid solution comprising a source of ions of a Group 2 and/or Group 3 metal. This combination of two solutions can take place under conditions sufficient to cause co-precipitation of the mixed oxide material as a solid from the liquid medium. Alternatively, the source of ions of the Group 4 metal and the source of ions of the Group 2 and/or Group 3 metal may be combined into a single solution. This solution may then be subjected to conditions sufficient to cause co-precipitation of a hydrated precursor of the solid mixed oxide material, such as by the addition of a precipitating reagent to the solution.

The temperature at which the liquid medium is maintained during the precipitation is generally less than about 200° C., such as in the range of from about 0° C. to about 200° C. A particular range of temperatures for precipitation is from about 20° C. to about 100° C. The resulting gel is preferably then hydrothermally treated at temperatures of at least 80° C., preferably at least 100° C. The hydrothermal treatment typically takes place in a vessel at atmospheric pressure. The gel, in one embodiment, is hydrothermally treated for up to 10 days, such as up to 5 days, for example up to 3 days.

The hydrated precursor to the metal oxide(s) is then recovered, for example by filtration or centrifugation, and washed and dried. The resulting material can then be calcined, such as in an oxidizing atmosphere, at a temperature of at least 400° C., such as at least 500° C., for example from about 600° C. to about 900° C., and particularly from about 650° C. to about 800° C., to form the active metal oxide or active mixed metal oxide. The calcination time is typically up to 48 hours, such as for about 0.5 to 24 hours, for example for about 1.0 to 10 hours. In one embodiment, calcination is carried out at about 700° C. for about 1 to about 3 hours.

In another embodiment, the Group 4 metal oxide and the Group 2 and/or Group 3 metal oxide are made separately and then contacted together to form the mixed metal oxide that is then contacted with the molecular sieve. For example, the Group 4 metal oxide can be contacted with the molecular sieve prior to introducing the Group 2 and/or Group 3 metal oxide or alternatively, the Group 2 and/or Group 3 metal oxide can be contacted with the molecular sieve prior to introducing the Group 4 metal oxide.

Where the catalyst composition comprises a Group 4 metal oxide and a Group 3 metal oxide, the mole ratio of the Group 4 metal oxide to the Group 3 metal oxide may be in the range of from 1000:1 to 1:1, such as from about 500:1 to 2:1, such as from about 100:1 to about 3:1, such as from about 75:1 to about 5:1 based on the total moles of the Group 4 and Group 3 metal oxides. In addition, the catalyst composition can contain from 1 to 25%, such as from 1 to 20%, such as from 1 to 15%, by weight of Group 3 metal based on the total weight of the mixed metal oxide, particularly where the Group 3 metal oxide is a lanthanum or yttrium metal oxide and the Group 4 metal oxide is a zirconium metal oxide.

Where the catalyst composition comprises a Group 4 metal oxide and a Group 2 metal oxide, the mole ratio of the Group 4 metal oxide to the Group 2 metal oxide may be in the range of from 1000:1 to 1:2, such as from about 500:1 to 2:3, such as from about 100:1 to about 1:1, such as from about 50:1 to about 2:1, based on the total moles of the Group 4 and Group 2 metal oxides. In addition, the catalyst composition can contain from 1 to 25%, such as from 1 to 20%, such as from 1 to 15%, by weight of Group 2 metal based on the total weight of the mixed metal oxide, particularly where the Group 2 metal oxide is calcium oxide and the Group 4 metal oxide is a zirconium metal oxide.

Catalyst Composition

The catalyst composition of the invention includes any one of the molecular sieves previously described and one or more of the active metal oxides described above, optionally with a binder and/or matrix material different from the active metal oxide(s). Typically, the weight ratio of the molecular sieve to the active metal oxide(s) in the catalyst composition is in the range of from 5 weight percent to 800 weight percent, such as from 10 weight percent to 600 weight percent, particularly from 20 weight percent to 500 weight percent, and more particularly from 30 weight percent to 400 weight percent.

There are many different binders that are useful in forming catalyst compositions. Non-limiting examples of binders that are useful alone or in combination include various types of hydrated alumina, silicas, and/or other inorganic oxide sols. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide binder component. For example, an alumina sol will convert to an aluminum oxide binder following heat treatment.

Aluminum chlorhydrol, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105–144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binder is an alumina sol, predominantly comprising aluminum oxide, optionally including some silicon. In yet another embodiment, the binder is peptized alumina made by treating an alumina hydrate, such as pseudobohemite, with an acid, preferably an acid that does not contain a halogen, to prepare a sol or aluminum ion solution. Non-limiting examples of commercially available colloidal alumina sols include Nalco 8676 available from Nalco Chemical Co., Naperville, Ill., and Nyacol AL20DW available from Nyacol Nano Technologies, Inc., Ashland, Mass.

Where the catalyst composition contains a matrix material, this is preferably different from the active metal oxide and any binder. Matrix materials are typically effective in reducing overall catalyst cost, acting as thermal sinks to assist in shielding heat from the catalyst composition for example during regeneration, densifying the catalyst composition, and increasing catalyst strength such as crush strength and attrition resistance.

Non-limiting examples of matrix materials include one or more non-active metal oxides including beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include subbentonites and those kaolins known as, for example, Dixie, McNamee, Georgia and Florida clays. Non-limiting examples of other matrix materials include haloysite, kaolinite, dickite, nacrite, or anauxite. The matrix material, such as a clay, may be subjected to well known modification processes such as calcination and/or acid treatment and/or chemical treatment.

In a preferred embodiment, the matrix material is a clay or a clay-type composition, particularly a clay or clay-type composition having a low iron or titania content, and most preferably the matrix material is kaolin. Kaolin has been found to form a pumpable, high solids content slurry, to have a low fresh surface area, and to pack together easily due to its platelet structure. A preferred average particle size of the matrix material, most preferably kaolin, is from about 0.1 μm to about 0.6 μm with a $D_{90}$ particle size distribution of less than about 1 μm.

Where the catalyst composition contains a binder or matrix material, the catalyst composition typically contains from about 1% to about 80%, such as from about 5% to about 60%, and particularly from about 5% to about 50%, by weight of the molecular sieve based on the total weight of the catalyst composition.

Where the catalyst composition contains a binder and a matrix material, the weight ratio of the binder to the matrix material is typically from 1:15 to 1:5, such as from 1:10 to 1:4, and particularly from 1:6 to 1:5. The amount of binder is typically from about 2% by weight to about 30% by weight, such as from about 5% by weight to about 20% by weight, and particularly from about 7% by weight to about 15% by weight, based on the total weight of the binder, the molecular sieve and matrix material. It has been found that a higher sieve content and lower matrix content increases the molecular sieve catalyst composition performance, whereas a lower sieve content and higher matrix content improves the attrition resistance of the composition.

The catalyst composition typically has a density in the range of from 0.5 g/cc to 5 g/cc, such as from from 0.6 g/cc to 5 g/cc, for example from 0.7 g/cc to 4 g/cc, particularly in the range of from 0.8 g/cc to 3 g/cc.

Method of Making the Catalyst Composition

In making the catalyst composition, the molecular sieve is first formed and is then physically mixed with the active metal oxide, preferably in a substantially dry, dried, or calcined state. Most preferably the molecular sieve and active metal oxides are physically mixed in their calcined state. Without being bound by any particular theory, it is believed that intimate mixing of the molecular sieve and one or more active metal oxides improves conversion processes using the molecular sieve composition and catalyst composition of the invention. Intimate mixing can be achieved by any method known in the art, such as mixing with a mixer muller, drum mixer, ribbon/paddle blender, kneader, or the like. Chemical reaction between the molecular sieve and the metal oxide(s) is unnecessary and, in general, is not preferred.

Where the catalyst composition contains a matrix and/or binder, the molecular sieve is conveniently initially formulated into a catalyst precursor with the matrix and/or binder and the active metal oxide is then combined with the formulated precursor. The active metal oxide can be added as unsupported particles or can be added in combination with a support, such as a binder or matrix material. The resultant catalyst composition can then be formed into useful shaped and sized particles by well-known techniques such as spray drying, pelletizing, extrusion, and the like.

In one embodiment, the molecular sieve composition and the matrix material, optionally with a binder, are combined with a liquid to form a slurry and then mixed, preferably rigorously mixed, to produce a substantially homogeneous mixture containing the molecular sieve composition. Non-limiting examples of suitable liquids include one or a combination of water, alcohol, ketones, aldehydes, and/or esters. The most preferred liquid is water. In one embodiment, the slurry is colloid-milled for a period of time sufficient to produce the desired slurry texture, sub-particle size, and/or sub-particle size distribution.

The molecular sieve composition and matrix material, and the optional binder, can be combined in the same or different liquids, and can be combined in any order, together, simultaneously, sequentially, or a combination thereof. In the preferred embodiment, the same liquid, preferably water is used. The molecular sieve composition, matrix material, and optional binder, are combined in a liquid as solids, substantially dry or in a dried form, or as slurries, together or separately. If solids are added together as dry or substantially dried solids, it is preferable to add a limited and/or controlled amount of liquid.

In one embodiment, the slurry of the molecular sieve composition, binder and matrix materials is mixed or milled to achieve a sufficiently uniform slurry of sub-particles of the molecular sieve catalyst composition that is then fed to a forming unit that produces the molecular sieve catalyst composition. In a preferred embodiment, the forming unit is spray dryer. Typically, the forming unit is maintained at a temperature sufficient to remove most of the liquid from the slurry, and from the resulting molecular sieve catalyst composition. The resulting catalyst composition when formed in this way takes the form of microspheres.

When a spray drier is used as the forming unit, typically, the slurry of the molecular sieve composition and matrix material, and optionally a binder, is co-fed to the spray drying volume with a drying gas with an average inlet temperature ranging from 200° C. to 550° C., and a combined outlet temperature ranging from 100° C. to about 225° C. In an embodiment, the average diameter of the spray dried formed catalyst composition is from about 40 µm to about 300 µm, such as from about 50 µm to about 250 µm, for example from about 50 µm to about 200 µm, and conveniently from about 65 µm to about 90 µm.

Other methods for forming a molecular sieve catalyst composition are described in U.S. patent application Ser. No. 09/617,714 filed Jul. 17, 2000 (spray drying using a recycled molecular sieve catalyst composition), which is herein incorporated by reference.

Once the molecular sieve catalyst composition is formed in a substantially dry or dried state, to further harden and/or activate the formed catalyst composition, a heat treatment such as calcination, at an elevated temperature is usually performed. Typical calcination temperatures are in the range from about 400° C. to about 1,000° C., such as from about 500° C. to about 800° C., such as from about 550° C. to about 700° C. Typical calcination environments are air (which may include a small amount of water vapor), nitrogen, helium, flue gas (combustion product lean in oxygen), or any combination thereof.

In a preferred embodiment, the catalyst composition is heated in nitrogen at a temperature of from about 600° C. to about 700° C. Heating is carried out for a period of time typically from 30 minutes to 15 hours, such as from 1 hour to about 10 hours, for example from about 1 hour to about 5 hours, and particularly from about 2 hours to about 4 hours.

Process for Using the Molecular Sieve Catalyst Compositions

The catalyst compositions described above are useful in a variety of processes including cracking, of for example a naphtha feed to light olefin(s) (U.S. Pat. No. 6,300,537) or higher molecular weight (MW) hydrocarbons to lower MW hydrocarbons; hydrocracking, of for example heavy petroleum and/or cyclic feedstock; isomerization, of for example aromatics such as xylene; polymerization, of for example one or more olefin(s) to produce a polymer product; reforming; hydrogenation; dehydrogenation; dewaxing, of for example hydrocarbons to remove straight chain paraffins; absorption, of for example alkyl aromatic compounds for separating out isomers thereof; alkylation, of for example aromatic hydrocarbons such as benzene and alkyl benzene, optionally with propylene to produce cumene or with long chain olefins; transalkylation, of for example a combination of aromatic and polyalkylaromatic hydrocarbons; dealkylation; hydrodecylization; disproportionation, of for example toluene to make benzene and paraxylene; oligomerization, of for example straight and branched chain olefin(s); and dehydrocyclization.

Preferred processes include processes for converting naphtha to highly aromatic mixtures; converting light olefin(s) to gasoline, distillates and lubricants; converting oxygenates to olefin(s); converting light paraffins to olefins and/or aromatics; and converting unsaturated hydrocarbons (ethylene and/or acetylene) to aldehydes for conversion into alcohols, acids and esters.

The most preferred process of the invention is a process directed to the conversion of a feedstock to one or more olefin(s). Typically, the feedstock contains one or more aliphatic-containing compounds such that the aliphatic moiety contains from 1 to about 50 carbon atoms, such as from 1 to 20 carbon atoms, for example from 1 to 10 carbon atoms, and particularly from 1 to 4 carbon atoms.

Non-limiting examples of aliphatic-containing compounds include alcohols such as methanol and ethanol, alkyl mercaptans such as methyl mercaptan and ethyl mercaptan, alkyl sulfides such as methyl sulfide, alkylamines such as methylamine, alkyl ethers such as dimethyl ether, diethyl ether and methylethyl ether, alkyl halides such as methyl chloride and ethyl chloride, alkyl ketones such as dimethyl ketone, formaldehydes, and various acids such as acetic acid.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) produced from the feedstock typically have from 2 to 30 carbon atoms, preferably 2 to 8 carbon atoms, more preferably 2 to 6 carbon atoms, still more preferably 2 to 4 carbons atoms, and most preferably are ethylene and/or propylene.

The catalyst composition of the invention is particularly useful in the process that is generally referred to as the gas-to-olefins (GTO) process or alternatively, the methanol-to-olefins (MTO) process. In this process, an oxygenated feedstock, most preferably a methanol-containing feedstock, is converted in the presence of a molecular sieve catalyst composition into one or more olefin(s), preferably and predominantly, ethylene and/or propylene.

Using the catalyst composition of the invention for the conversion of a feedstock, preferably a feedstock containing one or more oxygenates, the amount of olefin(s) produced based on the total weight of hydrocarbon produced is greater than 50 weight percent, typically greater than 60 weight percent, such as greater than 70 weight percent, and preferably greater than 80 weight percent. Moreover, the amount of ethylene and/or propylene produced based on the total weight of hydrocarbon product produced is greater than 40 weight percent, typically greater than 50 weight percent, for example greater than 65 weight percent, and preferably greater than 78 weight percent. Typically, the amount ethylene produced in weight percent based on the total weight of hydrocarbon product produced, is greater than 20 weight percent, such as greater than 30 weight percent, for example greater than 40 weight percent. In addition, the amount of propylene produced in weight percent based on the total weight of hydrocarbon product produced is typically greater than 20 weight percent, such as greater than 25 weight percent, for example greater than 30 weight percent, and preferably greater than 35 weight percent.

Using the catalyst composition of the invention for the conversion of a feedstock comprising methanol and dimethylether to ethylene and propylene, it is found that the production of ethane and propane is reduced by greater than 10%, such as greater than 20%, for example greater than 30%, and particularly in the range of from about 30% to 40% compared to a similar catalyst composition at the same conversion conditions but without the active metal oxide component(s).

In addition to the oxygenate component, such as methanol, the feedstock may contains one or more diluent(s), which are generally non-reactive to the feedstock or molecular sieve catalyst composition and are typically used to reduce the concentration of the feedstock. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, for example water, may be used either in a liquid or a vapor form, or a combination thereof. The diluent may be either added directly to the feedstock entering a reactor or added directly to the reactor, or added with the molecular sieve catalyst composition.

The present process can be conducted over a wide range of temperatures, such as in the range of from about 200° C. to about 1000° C., for example from about 250° C. to about 800° C., including from about 250° C. to about 750° C., conveniently from about 300° C. to about 650° C., typically from about 350° C. to about 600° C. and particularly from about 350° C. to about 550° C.

Similarly, the present process can be conducted over a wide range of pressures including autogenous pressure. Typically the partial pressure of the feedstock exclusive of any diluent therein employed in the process is in the range of from about 0.1 kPaa to about 5 MPaa, such as from about 5 kPaa to about 1 MPaa, and conveniently from about 20 kPaa to about 500 kPaa.

The weight hourly space velocity (WHSV), defined as the total weight of feedstock excluding any diluents per hour per weight of molecular sieve in the catalyst composition, typically ranges from about 1 hr-1 to about 5000 hr-1, such as from about 2 hr-1 to about 3000 hr-1, for example from about 5 hr-1 to about 1500 hr-1, and conveniently from about 10 hr-1 to about 1000 hr-1. In one embodiment, the WHSV is greater than 20 hr-1 and, where feedstock contains methanol and/or dimethyl ether, is in the range of from about 20 hr-1 to about 300 hr-1.

Where the process is conducted in a fluidized bed, the superficial gas velocity (SGV) of the feedstock including diluent and reaction products within the reactor system, and particularly within a riser reactor(s), is at least 0.1 meter per second (m/sec), such as greater than 0.5 m/sec, such as greater than 1 m/sec, for example greater than 2 m/sec, conveniently greater than 3 m/sec, and typically greater than 4 m/sec. See for example U.S. patent application Ser. No. 09/708,753 filed Nov. 8, 2000, which is herein incorporated by reference.

The process of the invention is conveniently conducted as a fixed bed process, or more typically as a fluidized bed process (including a turbulent bed process), such as a continuous fluidized bed process, and particularly a continuous high velocity fluidized bed process.

The process can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and Fluidization Engineering, D. Kunii and O. Levenspiel, Robert E. Krieger Publishing Company, New York, N.Y. 1977, which are all herein fully incorporated by reference.

The preferred reactor types are riser reactors generally described in Riser Reactor, Fluidization and Fluid-Particle Systems, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In one practical embodiment, the process is conducted as a fluidized bed process or high velocity fluidized bed process utilizing a reactor system, a regeneration system and a recovery system.

In such a process the reactor system would conveniently include a fluid bed reactor system having a first reaction zone within one or more riser reactor(s) and a second reaction zone within at least one disengaging vessel, typically comprising one or more cyclones. In one embodiment, the one or more riser reactor(s) and disengaging vessel are contained within a single reactor vessel. Fresh feedstock, preferably containing one or more oxygenates, optionally with one or more diluent(s), is fed to the one or more riser reactor(s) into which a molecular sieve catalyst composition or coked version thereof is introduced. In one embodiment, prior to being introduced to the riser reactor(s), the molecular sieve catalyst composition or coked version thereof is contacted with a liquid, preferably water or methanol, and/or a gas, for example, an inert gas such as nitrogen.

In an embodiment, the amount of fresh feedstock fed as a liquid and/or a vapor to the reactor system is in the range of from 0.1 weight percent to about 85 weight percent, such as from about 1 weight percent to about 75 weight percent, more typically from about 5 weight percent to about 65 weight percent based on the total weight of the feedstock including any diluent contained therein. The liquid and vapor feedstocks may be the same composition, or may contain varying proportions of the same or different feedstocks with the same or different diluents.

The feedstock entering the reactor system is preferably converted, partially or fully, in the first reactor zone into a gaseous effluent that enters the disengaging vessel along with the coked catalyst composition. In the preferred embodiment, cyclone(s) are provided within the disengaging vessel to separate the coked catalyst composition from the gaseous effluent containing one or more olefin(s) within the disengaging vessel. Although cyclones are preferred, gravity effects within the disengaging vessel can also be used to separate the catalyst composition from the gaseous effluent. Other methods for separating the catalyst composition from the gaseous effluent include the use of plates, caps, elbows, and the like.

In one embodiment, the disengaging vessel includes a stripping zone, typically in a lower portion of the disengaging vessel. In the stripping zone the coked catalyst composition is contacted with a gas, preferably one or a combination of steam, methane, carbon dioxide, carbon monoxide, hydrogen, or an inert gas such as argon, preferably steam, to recover adsorbed hydrocarbons from the coked catalyst composition that is then introduced to the regeneration system.

The coked catalyst composition is withdrawn from the disengaging vessel and introduced to the regeneration system. The regeneration system comprises a regenerator where the coked catalyst composition is contacted with a regeneration medium, preferably a gas containing oxygen, under conventional regeneration conditions of temperature, pressure and residence time.

Non-limiting examples of suitable regeneration media include one or more of oxygen, O3, SO3, N2O, NO, NO2, N2O5, air, air diluted with nitrogen or carbon dioxide, oxygen and water (U.S. Pat. No. 6,245,703), carbon monoxide and/or hydrogen. Suitable regeneration conditions are those capable of burning coke from the coked catalyst composition, preferably to a level less than 0.5 weight percent based on the total weight of the coked molecular sieve catalyst composition entering the regeneration system. For example, the regeneration temperature may be in the range of from about 200° C. to about 1500° C., such as from about 300° C. to about 1000° C., for example from about 450° C. to about 750° C., and conveniently from about 550° C. to 700° C. The regeneration pressure may be in the range of from about 15 psia (103 kPaa) to about 500 psia (3448 kPaa), such as from about 20 psia (138 kPaa) to about 250 psia (1724 kPaa), including from about 25 psia (172 kPaa) to about 150 psia (1034 kPaa), and conveniently from about 30 psia (207 kPaa) to about 60 psia (414 kPaa).

The residence time of the catalyst composition in the regenerator may be in the range of from about one minute to several hours, such as from about one minute to 100 minutes, and the volume of oxygen in the regeneration gas may be in the range of from about 0.01 mole percent to about 5 mole percent based on the total volume of the gas.

The burning of coke in the regeneration step is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated catalyst composition from the regeneration system and passing it through a catalyst cooler to form a cooled regenerated catalyst composition. The catalyst cooler, in an embodiment, is a heat exchanger that is located either internal or external to the regeneration system,. Other methods for operating a regeneration system are disclosed in U.S. Pat. No. 6,290,916 (controlling moisture), which is herein fully incorporated by reference.

The regenerated catalyst composition withdrawn from the regeneration system, preferably from a catalyst cooler, is combined with a fresh molecular sieve catalyst composition and/or re-circulated molecular sieve catalyst composition and/or feedstock and/or fresh gas or liquids, and returned to the riser reactor(s). In one embodiment, the regenerated catalyst composition withdrawn from the regeneration system is returned to the riser reactor(s) directly, preferably after passing through a catalyst cooler. A carrier, such as an inert gas, feedstock vapor, steam or the like, may be used, semi-continuously or continuously, to facilitate the introduction of the regenerated catalyst composition to the reactor system, preferably to the one or more riser reactor(s).

By controlling the flow of the regenerated catalyst composition or cooled regenerated catalyst composition from the regeneration system to the reactor system, the optimum level of coke on the molecular sieve catalyst composition entering the reactor is maintained. There are many techniques for controlling the flow of a catalyst composition described in Michael Louge, Experimental Techniques, Circulating Fluidized Beds, Grace, Avidan and Knowlton, eds., Blackie, 1997 (336–337), which is herein incorporated by reference.

Coke levels on the catalyst composition are measured by withdrawing the catalyst composition from the conversion process and determining its carbon content. Typical levels of coke on the molecular sieve catalyst composition, after regeneration, are in the range of from 0.01 weight percent to about 15 weight percent, such as from about 0.1 weight percent to about 10 weight percent, for example from about 0.2 weight percent to about 5 weight percent, and conveniently from about 0.3 weight percent to about 2 weight percent based on the weight of the molecular sieve.

The gaseous effluent is withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment, for example various condensers, heat exchangers, refrigeration systems or chill trains, compressors, knock-out drums or pots, pumps, and the like.

Non-limiting examples of these towers, columns, splitters or trains used alone or in combination include one or more of a demethanizer, preferably a high temperature demethanizer, a de-ethanizer, a depropanizer, a wash tower often referred to as a caustic-wash tower and/or quench tower, absorbers, adsorbers, membranes, ethylene (C2) splitter, propylene (C3) splitter, butene (C4) splitter, and the like.

Various recovery systems useful for recovering predominantly olefin(s), preferably light olefin(s) such as ethylene, propylene and/or butene, are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Other recovery systems that include purification systems, for example for the purification of olefin(s), are described in Kirk-Othmer Encyclopedia of Chemical Technology, 4th Edition, Volume 9, John Wiley & Sons, 1996, pages 249–271 and 894–899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which are herein incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Typically, in converting one or more oxygenates to olefin(s) having 2 or 3 carbon atoms, a minor amount hydrocarbons, particularly olefin(s), having 4 or more carbon atoms is also produced. The amount of C4+hydrocarbons is normally less than 20 weight percent, such as less than 10 weight percent, for example less than 5 weight percent, and particularly less than 2 weight percent, based on the total weight of the effluent gas withdrawn from the process, excluding water. Typically, therefore the recovery system may include one or more reaction systems for converting the C4+impurities to useful products.

Non-limiting examples of such reaction systems are described in U.S. Pat. No. 5,955,640 (converting a four carbon product into butene-1), U.S. Pat. No. 4,774,375 (isobutane and butene-2 oligomerized to an alkylate gasoline), U.S. Pat. No. 6,049,017 (dimerization of n-butylene), U.S. Pat. Nos. 4,287,369 and 5,763,678 (carbonylation or hydroformulation of higher olefins with carbon dioxide and hydrogen making carbonyl compounds), U.S. Pat. No.4,542,252 (multistage adiabatic process), U.S. Pat. No. 5,634,354 (olefin-hydrogen recovery), and Cosyns, J. et al., Process for Upgrading C3, C4 and C5 Olefinic Streams, Pet. & Coal, Vol. 37, No. 4 (1995) (dimerizing or oligomerizing propylene, butylene and pentylene), which are all herein fully incorporated by reference.

The preferred light olefin(s) produced by any one of the processes described above are high purity prime olefin(s) products that contain a single carbon number olefin in an amount greater than 80 percent, such as greater than 90 weight percent, such as greater than 95 weight percent, for example at least about 99 weight percent, based on the total weight of the olefin.

In one practical embodiment, the process of the invention forms part of an integrated process for producing light olefin(s) from a hydrocarbon feedstock, preferably a gaseous hydrocarbon feedstock, particularly methane and/or ethane. The first step in the process is passing the gaseous feedstock, preferably in combination with a water stream, to a syngas production zone to produce a synthesis gas (syngas) stream, typically comprising carbon dioxide, carbon monoxide and hydrogen. Syngas production is well known, and typical syngas temperatures are in the range of from about 700° C. to about 1200° C. and syngas pressures are in the range of from about 2 MPa to about 100 MPa. Synthesis gas streams are produced from natural gas, petroleum liquids, and carbonaceous materials such as coal, recycled plastic, municipal waste or any other organic material. Preferably synthesis gas stream is produced via steam reforming of natural gas.

The next step in the process involves contacting the synthesis gas stream generally with a heterogeneous catalyst, typically a copper based catalyst, to produce an oxygenate containing stream, often in combination with water. In one embodiment, the contacting step is conducted at temperature in the range of from about 150° C. to about 450° C. and a pressure in the range of from about 5 MPa to about 10 MPa.

This oxygenate containing stream, or crude methanol, typically contains the alcohol product and various other components such as ethers, particularly dimethyl ether, ketones, aldehydes, dissolved gases such as hydrogen methane, carbon oxide and nitrogen, and fuel oil. The oxygenate containing stream, crude methanol, in the preferred embodiment is passed through a well known purification processes, distillation, separation and fractionation, resulting in a purified oxygenate containing stream, for example, commercial Grade A and AA methanol.

The oxygenate containing stream or purified oxygenate containing stream, optionally with one or more diluents, can then be-used as a feedstock in a process to produce light olefin(s), such as ethylene and/or propylene. Non-limiting examples of this integrated process are described in EP-B-0 933 345, which is herein fully incorporated by reference.

In another more fully integrated process, that optionally is combined with the integrated processes described above, the olefin(s) produced are directed to, in one embodiment, one or more polymerization processes for producing various polyolefins. (See for example U.S. patent application Ser. No. 09/615,376 filed Jul. 13, 2000, which is herein fully incorporated by reference.)

Polymerization processes include solution, gas phase, slurry phase and a high pressure processes, or a combination thereof. Particularly preferred is a gas phase or a slurry phase polymerization of one or more olefin(s) at least one of which is ethylene or propylene. These polymerization processes utilize a polymerization catalyst that can include any one or a combination of the molecular sieve catalysts discussed above, however, the preferred polymerization catalysts are the Ziegler-Natta, Phillips-type, metallocene, metallocene-type and advanced polymerization catalysts, and mixtures thereof.

In a preferred embodiment, the integrated process comprises a process for polymerizing one or more olefin(s) in the presence of a polymerization catalyst system in a polymerization reactor to produce one or more polymer products, wherein the one or more olefin(s) have been made by converting an alcohol, particularly methanol, using a molecular sieve catalyst composition as described above. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

The polymers produced by the polymerization processes described above include linear low density polyethylene, elastomers, plastomers, high density polyethylene, low density polyethylene, polypropylene and polypropylene copolymers. The propylene based polymers produced by the polymerization processes include atactic polypropylene, isotactic polypropylene, syndiotactic polypropylene, and propylene random, block or impact copolymers.

EXAMPLES

In order to provide a better understanding of the present invention including representative advantages thereof, the following Examples are offered.

In the Examples, LEI is defined as the ratio of the lifetime of a molecular sieve catalyst composition containing an active metal oxide(s) compared to that of the same molecular sieve in the absence of a metal oxide, defined as having an LEI of 1. For the purpose of determining LEI, lifetime is defined as the cumulative amount of oxygenate converted, preferably into one or more olefin(s), per gram of molecular sieve, until the conversion rate drops to about 10% of its initial value. If the conversion has not fallen to 10% of its initial value by the end of the experiment, lifetime is estimated by linear extrapolation based on the rate of decrease in conversion over the last two data points in the experiment. For the purposes of determining the LEI for the following Examples in a preferred oxygenate conversion process, methanol is converted to one or more olefin(s) at 475° C., 25 psig (172 kPag) and a methanol weight hourly space velocity of 100 h−1.

"Prime Olefin" is the sum of the selectivity to ethylene and propylene. The ratio "C2=/C3=" is the ratio of the ethylene to propylene selectivity weighted over the run. The "C3 Purity" is calculated by dividing the propylene selectivity by the sum of the propylene and propane selectivities. The selectivities for methane, ethylene, ethane, propylene, propane, C4's and C5+'s are average selectivities weighted over the run. Note that the C5+'s consist only of C5's, C6's and C7's. The selectivity values do not sum to 100% in the Tables because they have been corrected for coke as is well known.

Example A

Preparation of Molecular Sieve

A silicoaluminophosphate molecular sieve, SAPO-34, designated as MSA, was crystallized in the presence of tetraethyl ammonium hydroxide (R1) and dipropylamine (R2) as the organic structure directing agents or templating agents. A mixture of the following mole ratio composition:

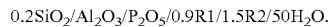

$0.2SiO_2/Al_2O_3/P_2O_5/0.9R1/1.5R2/50H_2O.$ was prepared by initially mixing an amount of Condea Pural SB with deionised water, to form a slurry. To this slurry was added an amount of phosphoric acid (85%). These additions were made with stirring to form a homogeneous mixture. To this homogeneous mixture Ludox AS40 (40% of SiO2) was added, followed by the addition of R1 with mixing to form a homogeneous mixture. To this homogeneous mixture R2 was added. This homogeneous mixture was then crystallized with agitation in a stainless steel autoclave by heating to 170° C. for 40 hours. This provided a slurry of the crystalline molecular sieve. The crystals were then separated from the mother liquor by filtration. The molecular sieve crystals were then mixed with a binder and matrix material and formed into particles by spray drying.

Example B

Conversion Process

All catalytic or conversion data presented was obtained using a microflow reactor consisting of a stainless steel reactor (¼ inch (0.64 cm) outer diameter) located in a furnace to which vaporized methanol was fed. The reactor was maintained at a temperature of 475° C. and a pressure of 25 psig (172.4 kPag) The flow rate of the methanol was such that the flow rate of methanol on weight basis per gram of molecular sieve, also known as the weight hourly space velocity (WHSV) was 100 h−1. Product gases exiting the reactor were collected and analyzed using gas chromatography. The catalyst load in each experiment was 50 mg and the reactor bed was diluted with quartz to minimize hot spots in the reactor. In particular, for the catalyst composition of the invention, a physical mixture of the MSA molecular sieve of Example A and the active metal oxide(s) was used. The total catalyst composition load remained 50 mg, and the methanol flow rate was adjusted as the amount of molecular sieve in the reactor bed was reduced by the addition of the mixed metal oxide such that the methanol WHSV was 100 h−1 based on the amount of molecular sieve in the reactor bed.

Example 1

One thousand grams of ZrOCl2.8H2O was dissolved with stirring in 3.0 liters of distilled water. Another solution containing 400 grams of concentrated NH4OH and 3.0 liters of distilled water was prepared. Both solutions were heated to 60° C. These two heated solutions were combined at a rate of 50ml/min using nozzle mixing. The pH of the final composite was adjusted to approximately 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this product was calcined to 700° C. in flowing air for 3 hours to produce an active zirconium oxide material.

Example 2

Five hundred grams of ZrOCl2.8H2O and 84 grams of La(NO3)3.6H2O were dissolved with stirring in 3.0 liters of distilled water. Another solution containing 260 grams of concentrated NH4OH and 3.0 liters of distilled water was prepared. Both solutions were heated to 60° C. and then combined at the rate of 50 ml/min using nozzle mixing to form the final mixture, a slurry. The pH of the final mixture was adjusted to approximately 9 by the addition of concentrated ammonium hydroxide. This slurry was then put in a polypropylene bottle and placed in a steam box (100° C.) for 72 hours. The resulting product formed was recovered by filtration, washed with excess-water, and dried overnight at 85° C. A portion of this product, was calcined to 700° C. in flowing air for 3 hours to produce an active mixed metal oxide containing a nominal 10 weight percent La (lanthanum) based on the final weight of the mixed metal oxide.

Example 3

Fifty grams of ZrOCl2.8H2O were dissolved with stirring in 300 ml of distilled water. Another solution containing 4.2 grams of La(NO3)3.6H2O and 300 ml of distill water was prepared. These two solutions were combined with stirring to form a final mixture. The pH of the final mixture, a slurry, was adjusted to approximately 9 by the addition of concentrated ammonium hydroxide (28.9 grams). This slurry was then put in a polypropylene bottle and placed in a steam box (100° C.) for 72 hours. The resulting product formed was recovered by filtration, washed with excess water, and dried overnight at 85° C. A portion of this resulting product was calcined to 700° C. in flowing air for 3 hours to produce an active mixed metal oxide containing a nominal 5 weight percent La based on the final weight of the mixed metal oxide.

Example 4

Five hundred grams of ZrOCl2.8H2O and 70 grams of Y(NO3)3.5H2O were dissolved with stirring in 3.0 liters of distilled water. Another solution containing 260 grams of concentrated NH4OH and 3.0 liters of distilled water was prepared. Both solutions were heated to 60° C. and then combined at the rate of 50 ml/min using nozzle mixing to form a final mixture. The pH of the final mixture, a slurry, was adjusted to approximately 9 by the addition of concentrated ammonium hydroxide. This slurry was then put in a polypropylene bottle and placed in a steam box (100° C.) for 72 hours. The resulting product formed was recovered by filtration, washed with excess water, and dried overnight at 85° C. A portion of the resulting product was calcined to 700° C. in flowing air for 3 hours to produce an active mixed metal oxide containing a nominal 10 weight percent Y (yttrium) based on the final weight of the mixed metal oxide.

Example 5

Five hundred grams of ZrOCl2.8H2O and 56 grams of Ca(NO3)2.4H2O were dissolved with stirring in 3000 ml of distilled water. Another solution containing 260 grams of NH4OH and 3000 ml of distilled water was prepared. These two solutions were combined with stirring. The pH of the final composite was adjusted to approximately 9 by the addition of concentrated ammonium hydroxide (160 grams). This slurry was then put in polypropylene bottles and placed in a steambox (100° C.) for 72 hours. The resulting product formed was recovered by filtration, washed with excess water, and dried overnight at 85° C. A portion of this product was calcined to 700° C. in flowing air for 3 hours to produce an active mixed metal oxide containing a nominal 5 weight percent Ca (calcium) based on the final weight of the mixed metal oxide.

Example 6

Seventy grams of $TiOSO_4.xH_2SO_4.xH_2O(x=1)$ were dissolved with stirring in 400 ml of distilled water. Another solution containing 12.8 grams of $CeSO_4$ and 300 ml of distilled water was prepared. These two solutions were combined with stirring. The pH of the final composite was adjusted to approximately 8 by the addition of concentrated ammonium hydroxide (64.3 grams). This slurry was then put in polypropylene bottles and placed in a steambox (100° C.) for 72 hours. The product formed was recovered by filtration, washed with excess water, and dried overnight at 85° C. A portion of this product was calcined to 700° C. in flowing air for 3 hours to produce an active mixed metal oxide containing a nominal 5 weight percent Ce based on the final weight of the mixed metal oxide.

Example 7

Five grams of $HfOCl_2.xH_2O$ was dissolved with stirring in 100 ml of distilled water. The pH of the final composite was adjusted to approximately 9 by the addition of concentrated ammonium hydroxide (4.5 grams). This slurry was then put in a polypropylene bottle and placed in a steambox (100° C.) for 72 hours. The product formed was recovered by filtration, washed with excess water, and dried overnight at 85° C. A portion of this catalyst was calcined to 700° C. in flowing air for 3 hours to produce an active hafnium oxide.

Example 8

Five grams of $HfOCl_2.xH_2O$ and 0.62 grams of $La(NO_3)_3.6H_2O$ were dissolved with stirring in 100 ml of distilled water. The pH of the final composite was adjusted to approximately 9 by the addition of concentrated ammonium hydroxide (3.5 grams). This slurry was then put in a polypropylene bottle and placed in a steambox (100° C.) for 72 hours. The product formed was recovered by filtration, washed with excess water, and dried overnight at 85° C. A portion of this catalyst was calcined to 700° C. in flowing air for 3 hours to produce an active mixed metal oxide containing a nominal 5 weight % La based on the final weight of the mixed metal oxide.

Example 9

The carbon dioxide uptake of the oxides of Examples 1 through 8 were measured using a Mettler TGA/SDTA 851 thermogravimetric analysis system under ambient pressure. The metal oxide samples were first dehydrated in flowing air to about 500° C. for one hour after which the uptake of carbon dioxide was measured at 100° C. The surface area of the samples were measured in accordance with the method of Brunauer, Emmett, and Teller (BET) to provide the carbon dioxide uptake in terms of mg carbon dioxide/$m^2$ of the metal oxide presented in Table 1.

TABLE 1

| Example | Catalyst Dry Weight (mg) | mg of $CO_2$ | Surface Area ($m^2/g$) | $CO_2$ Uptake (mg of $CO_2/m^2$) |
|---|---|---|---|---|
| 1 | 76 | 0.0980 | 29 | 0.045 |
| 2 | 115 | 0.7781 | 80 | 0.085 |
| 3 | 73 | 0.4243 | 89 | 0.065 |
| 4 | 97 | 0.3808 | 100 | 0.039 |
| 5 | 78 | 0.5399 | 85 | 0.081 |
| 6 | 43 | 0.1035 | 50 | 0.048 |
| 7 | 158 | 0.3704 | 25 | 0.094 |
| 8 | 164 | 0.7359 | 60 | 0.075 |

Example 10 (Comparative)

The performance of the control, the molecular sieve of Example A, MSA, using a 50 mg load in the reactor and under the conditions discussed above in Example B is reported in Tables 2 and 3.

Example 11

In this Example, the catalyst composition consisted of 40 mg MSA of Example A and 10 mg of the active zirconium oxide of Example 1. The catalyst composition and active mixed metal oxide were well mixed, and then diluted with quarts to form the reactor bed. The results of testing this catalyst composition in the process of Example B are shown in Tables 2 and 3. The results indicate that the addition of the active zirconium oxide to the catalyst bed increased the lifetime of the molecular sieve composition significantly, and decreased the amounts of undesired ethane and propane.

Example 12

In this Example, the catalyst composition consisted of 40 mg MSA of Example A and 10 mg of the active mixed metal oxide containing 10 weight percent La, described in Example 2. The catalyst composition and active mixed metal oxide were well mixed, and then diluted with quartz to form the reactor bed. The results of testing this catalyst composition in the process of Example B are shown in Tables 2 and 3. The data in Tables 2 and 3 illustrate that by constituting 20% of the catalyst composition load with the active mixed metal oxide containing 10 weight percent La, the lifetime of the molecular sieve doubled, as indicated by its LEI value of 2. In addition, there was a net gain of 1.7% in prime olefins on an absolute basis, with most of this gain being due to an increase in propylene of 2.76%, offsetting a small decrease in ethylene of 1.07%. Selectivity to ethane decreased by 39% and selectivity to propane decreased by 37% suggesting that hydrogen transfer reactions have been significantly reduced.

Example 13

In this Example, the catalyst consisted of 30 mg MSA of Example A and 20 mg of the active mixed metal oxide containing 10 weight percent La, as described in Example 2. The catalyst composition and active mixed metal oxide were well mixed, and then diluted with quartz to form the reactor bed. The results of testing this catalyst composition in the process of Example B are shown in Tables 2 and 3. The data of Tables 2 and 3 illustrate that by constituting 40% of the catalyst composition load containing 10 weight percent La, the lifetime of the SAPO-34 catalyst composition increased by 440%. Trends in selectivity for this catalyst loading are similar to those seen in Example 8.

Example 14

In this Example, the catalyst composition consisted of 40 mg MSA from Example A and 10 mg of the active mixed metal oxide containing 10 weight percent Y, as described in Example 4. The catalyst composition and active mixed metal oxide were well mixed, and then diluted with quartz to form the reactor bed. The results of testing this catalyst composition in the process of Example B are shown in Tables 2 and 3. The substitution of yttrium for lanthanum has the effect of increasing the LEI even further. However, the improvements in selectivity are not as dramatic as seen with the lanthanum, with the gain in prime olefin being 1.2% on an absolute basis.

Example 15

In this Example, the catalyst consisted of 40 mg MSA of Example A and 10 mg of the active mixed metal oxide containing 5 weight percent La, as described in Example 3. The catalyst composition and active mixed metal oxide were well mixed, and then diluted with quartz to form the reactor bed. The results of testing this catalyst composition in the process of Example B are shown in Tables 2 and 3. It will be seen that the active mixed metal oxide containing 5 weight percent lanthanum oxide seems to have a much stronger effect in increasing the LEI than the active mixed metal oxide of Example 8 containing 10 weight percent La.

Example 16

In this Example 16, the catalyst consisted of 40 mg MSA of Example A and 10 mg of an active mixed metal oxide containing 5 weight percent Ca, as described in Example 5. The catalyst composition and active mixed metal oxide were well mixed, and then diluted with quartz to form the reactor bed. The results of this experiment in the reactor and conditions discussed above in Example B are shown in Tables 2 and 3. The active mixed metal oxide containing 5 weight percent calcium oxide has increased the lifetime of the molecular sieve composition by 223%.

Example 17 (Comparative)

In this Comparative Example, the catalyst composition consisted of 40 mg MSA of Example A and 10 mg of an amorphous silica/alumina, an inactive mixed metal oxide. The molecular sieve catalyst composition and the inactive mixed metal oxide catalysts were well mixed, and then diluted with quartz to form the reactor bed. The results of testing this catalyst composition in the process of Example B are also shown in Tables 2 and 3. This Comparative Example 17 illustrates a reduction in LEI to a value less than 1.0 when an inactive mixed metal oxide is utilized as compared to Example 11 of the invention. In addition, there is a loss of 1.07% in prime olefin selectivity, and no significant reduction in ethane and propane production.

Example 18

In this Example, the catalyst composition consisted of 40 mg MSA from Example A and 10 mg an active mixed metal oxide containing Ce and titania, as described in Example 6. The catalyst composition and active mixed metal oxide were well mixed, and then diluted with quartz to form the reactor bed. The results of testing this catalyst composition in the process of Example B are shown in Tables 2 and 3. The presence of the active mixed metal oxide increased the lifetime of the molecular sieve composition by 134%.

Example 19

In this Example, the catalyst composition consisted of 40 mg MSA of Example A and 10 mg of the active hafnium metal oxide described in Example 7. The catalyst composition and active metal oxide were well mixed, and then diluted with quartz to form the reactor bed. The results of testing this catalyst composition in the process of Example B are shown in Tables 2 and 3. The data in Tables 2 and 3 illustrate that by constituting 20% of the catalyst composition load with the active hafnium metal oxide, the lifetime of the molecular sieve has increased by 126%. Selectivity to ethane decreased by 40% and selectivity to propane decreased by 46% suggesting that hydrogen transfer reactions have been significantly reduced.

Example 20

In this Example, the catalyst composition consisted of 40 mg MSA of Example A and 10 mg of the active mixed metal oxide containing 5 weight percent La, described in Example 8. The catalyst composition and active mixed metal oxide were well mixed, and then diluted with quartz to form the reactor bed. The results of testing this catalyst composition in the process of Example B are shown in Tables 2 and 3.

The data in Tables 2 and 3 illustrate that by constituting 20% of the catalyst composition load with the active mixed metal oxide containing 5 weight percent La, the lifetime of the molecular sieve has increased by 150%. Selectivity to ethane decreased by 51% and selectivity to propane decreased by 51% suggesting that hydrogen transfer reactions have been significantly reduced.

TABLE 2

| Example | Reactor Bed Composition (wt %) | LEI | Prime Olefin (%) | $C_2^-/C_3^-$ | $C_3$ Purity (%) |
|---|---|---|---|---|---|
| 10 (Comp) | 100% MSA | 1 | 74.65 | 0.92 | 92.7 |
| 11 | 80% MSA/20% $ZrO_2$ | 2.64 | 74.79 | 0.82 | 96.1 |
| 12 | 80% MSA/20% of 10% La/$ZrO_2$ | 2.03 | 76.34 | 0.84 | 95.6 |
| 13 | 60% MSA/40% of 10% La/$ZrO_2$ | 5.41 | 75.50 | 0.85 | 94.6 |
| 14 | 80% MSA/20% of 10% Y/$ZrO_2$ | 2.79 | 75.81 | 0.85 | 94.9 |
| 15 | 80% MSA/20% of 5% La/$ZrO_2$ | 4.85 | 75.84 | 0.84 | 94.8 |
| 16 | 80% MSA/20% of 5% Ca/$ZrO_2$ | 3.23 | 73.85 | 0.79 | 96.7 |
| 17 (Comp) | 80% MSA/20% of $SiO_2/Al_2O_3$ | 0.79 | 73.58 | 0.93 | 93.3 |
| 18 | 80% MSA/20% of Ce/$TiO_2$ | 2.34 | 65.65 | 0.87 | 95.1 |
| 19 | 80% MSA/20% of $HfO_2$ | 2.26 | 72.98 | 0.71 | 96.2 |
| 20 | 80% MSA/20% of 5% La/$HfO_2$ | 2.50 | 72.75 | 0.76 | 96.5 |

TABLE 3

| Example | Reactor Bed (wt %) | Product Selectivities (%) | | | | | | |
|---|---|---|---|---|---|---|---|---|
| | | $CH_4$ | $C_2^-$ | $C_2^°$ | $C_3^-$ | $C_3^°$ | $C_4's^-$ | $C_5+$ |
| 10 (Comp) | 100% MSA | 1.51 | 35.82 | 0.95 | 38.83 | 3.05 | 14.50 | 2.12 |
| 11 | 80% MSA/20% $ZrO_2$ | 1.50 | 33.74 | 0.53 | 41.05 | 1.68 | 14.79 | 3.31 |
| 12 | 80% MSA/20% of 10% La/$ZrO_2$ | 1.31 | 34.75 | 0.58 | 41.59 | 1.93 | 14.96 | 2.46 |
| 13 | 60% MSA/40% of 10% La/$ZrO_2$ | 1.47 | 34.75 | 0.66 | 40.75 | 2.32 | 14.76 | 2.52 |
| 14 | 80% MSA/20% of 10% Y/$ZrO_2$ | 1.32 | 34.92 | 0.66 | 40.88 | 2.20 | 14.41 | 3.07 |
| 15 | 80% MSA/20% of 5% La/$ZrO_2$ | 1.26 | 34.59 | 0.64 | 41.25 | 2.28 | 14.96 | 2.52 |
| 16 | 80% MSA/20% of 5% Ca/$ZrO_2$ | 1.50 | 32.65 | 0.42 | 41.20 | 1.43 | 14.84 | 5.34 |
| 17 (Comp) | 80% MSA/20% of $SiO_2/Al_2O_3$ | 2.17 | 35.46 | 0.89 | 38.12 | 2.72 | 14.21 | 2.65 |
| 18 | 80% MSA/20% of Ce/$TiO_2$ | 6.79 | 30.57 | 0.75 | 35.09 | 1.80 | 12.72 | 3.97 |
| 19 | 80% MSA/20% of $HfO_2$ | 1.98 | 31.62 | 0.52 | 41.36 | 1.65 | 14.64 | 4.93 |
| 20 | 80% MSA/20% of 5% La/$HfO_2$ | 1.98 | 31.58 | 0.47 | 41.18 | 1.49 | 14.53 | 5.52 |

While the present invention has been described and illustrated by to particular embodiments, those of ordinary skill in the art will e that the invention lends itself to variations not necessarily illustrated or example, it is contemplated that the molecular sieve compositions described herein are useful as absorbents, adsorbents, gas separators, detergents, water purifiers, and for other various uses such as agriculture and horticulture. It is within the scope of this invention to add one or more active metal oxide(s) to the synthesis mixture for making a molecular sieve as described above. For this reason, then, reference should be made solely to the appended claims for purposes of determining the true scope of the present invention.

We claim:

1. A process for converting a feedstock comprising contacting oxygenates, naphthas, alkyl mercaptans, alkyl sulfides, alkyl amines or alkyl halides, with a catalyst composition comprising a molecular sieve and an Group 4 metal oxide having an uptake of carbon dioxide at 100° C. of at least 0.03 mg/m$^2$ of the metal oxide to form one or more olefins.

2. The process of claim 1 wherein said metal oxide has an uptake of carbon dioxide at 100° C. of at least 0.035 mg/m$^2$ of the metal oxide.

3. The process of claim 1 wherein said metal oxide has an uptake of carbon dioxide at 100° C. of less than 10 mg/m$^2$ of the metal oxide.

4. The process of claim 1 wherein said metal oxide has an uptake of carbon dioxide at 100° C. of less than 5 mg/m$^2$ of the metal oxide.

5. The process of claim 2 and also including at least one of a binder and a matrix material different from said metal oxide.

6. The process of claim 2 and also including a binder and a matrix material each being different from one another and from said metal oxide.

7. The process of claim 6 wherein the binder is an alumina sol.

8. The process of claim 6 wherein the matrix is a clay.

9. The process of claim 1 wherein the catalyst composition has a Lifetime Enhancement Index (LET) greater than 1.

10. The process of claim 1 wherein the molecular sieve is synthesized from reaction mixture comprising at least two of a silicon source, a phosphorus source and an aluminum source, optionally in the presence of a templating agent.

11. The process of claim 1 wherein the molecular sieve is a silicoaluminophosphate.

12. The process of claim 1 wherein the catalyst composition also includes a calcined Group 2 and/or Group 3 metal oxide.

13. The process of claim 1 wherein the feedstock comprises methanol and/or dimethylether.

14. A process for convening feedstock comprising contacting oxygenates, naphthas, alkyl mercaptans, alkyl sulfides, alkyl amines or alkyl halides, with a catalyst composition prepared by a method of making the catalyst composition, to form one or more olefins, the method comprising physically mixing first particles comprising a molecular sieve with second particles comprising a Group 4 metal oxide having an uptake of carbon dioxide at 100° C. of at least 0.03 mg/m$^2$ of the metal oxide particles.

15. A process for converting feedstock comprising contacting oxygenates, naphthas, alkyl mercaptans, alkyl sulfides, alkyl amines or alkyl halides, with a catalyst composition to form one or more olefins, the catalyst composition having been prepared by
   (i) synthesizing a molecular sieve from a reaction mixture comprising at least one templating agent and at least two of a silicon source, a phosphorus source and an aluminum source; and
   (ii) recovering the molecular sieve synthesized in (i);
   (iii) forming a hydrated precursor of a Group 4 metal oxide by precipitation from a solution containing a source of Group 4 metal ions;
   (iv) recovering the hydrated precursor formed in (iii);
   (v) calcining the hydrated precursor recovered (iv) to form a calcined Group 4 metal oxide that has an uptake of carbon dioxide at 100° C. of at least 0.03 mg/m$^2$ of the metal oxide; and
   (vi) physically mixing the molecular sieve recovered in (i) and the calcined metal oxide produced in (v).

16. A process for producing one or more olefin(s), the process comprising:
   (a) contacting a feedstock comprising at least one oxygenate in a reactor system with a catalyst composition comprising a molecular sieve, a binder, a matrix material, and a calcined Group 4 metal oxide under conditions sufficient to form one or more olefins;
   (b) withdrawing from the reactor system an effluent stream containing the one or more olefins; and
   (c) passing the effluent stream through a recovery system; and
   (d) recovering at least the one or more olefin(s).

17. The process of claim 16 wherein the binder is an alumina sol.

18. The process of claim 16 wherein the matrix material is a clay.

19. The process of claim 16 wherein the molecular sieve is a silicoaluminophosphate molecular sieve and/or an aluminophosphate molecular sieve.

20. The process of claim 16 wherein the Group 4 metal oxide is a zirconium metal oxide or a hafnium metal oxide or a mixture thereof.

21. The process of claim 16 wherein the Group 4 metal oxide has an uptake of carbon dioxide at 100° C. of at least 0.03 mg/m$^2$ of the metal oxide.

22. The process of claim 16 wherein the catalyst composition also includes a calcined Group 2 and/or Group 3 metal oxide.

23. The process of claim 16 wherein the feedstock comprises methanol and/or dimethylether.

24. The process of claim 16 wherein the Group 4 metal oxide has a surface area greater than 10 m$^2$/g.

25. The process of claim 16 wherein the LEI of the catalyst composition is greater than that for the same catalyst composition without the Group 4 metal oxide.

26. The process of claim 16 wherein the sieve catalyst composition has an LEI greater than 1.5.

* * * * *